United States Patent [19]

Hiramitsu et al.

[11] Patent Number: 5,202,244

[45] Date of Patent: Apr. 13, 1993

[54] PROCESS FOR PRODUCING APHIDICOLIN USING THE MICRORGANISM VERTICILLIUM SP

[75] Inventors: Tokiyuki Hiramitsu; Atsushi Mouri; Nobuyoshi Niizuma, all of Kitaibaraki, Japan

[73] Assignee: Nippon Mektron Limited, Tokyo, Japan

[21] Appl. No.: 731,876

[22] Filed: Jul. 18, 1991

[30] Foreign Application Priority Data

Aug. 8, 1990 [JP] Japan .................................. 2-209557

[51] Int. Cl.⁵ .............................................. C12P 7/02
[52] U.S. Cl. .................................... 435/132; 435/171; 435/254; 435/911
[58] Field of Search ................ 435/171, 911, 132, 254

[56] References Cited

PUBLICATIONS

Starratt et al., "The Production of Aphidicolin by Nigrospora sphaerica", Can. J. Microbiol., vol. 20, pp. 416–417, 1974.

Fisher, P. J. et al., "Onychophora Coprophila-A New Fungus Producing Aphidicolin", Trans. Br. Mycol. Soc., vol. 83, No. 1, pp. 149–150, 1984.

Kawada, K. et al., "Isolation of Aphidicolin as an Root Growth Inhibitor from Harziella entomophilla", Agric. Biol. Chem., vol. 48, No. 8, pp. 1611-1612 1978.

Clayton, N. et al., "Insecticidal Secondary Metabolic Products From the Entomagenous Fungus Verticillium lecanii", J. Invertebr. Pathol., vol. 40, No. 3, pp. 413–418, 1982.

Primary Examiner—Douglas W. Robinson
Assistant Examiner—Marian C. Knode
Attorney, Agent, or Firm—Fred Philpitt

[57] ABSTRACT

Aphidicolin is produced with a high productivity by culturing microorganisms belonging to the genus Verticillium, for example, Verticillium sp FERM BP-3430, in a culture medium, thereby forming and accumulating aphidicolin therein and recovering the aphidicolin therefrom.

1 Claim, 2 Drawing Sheets

50 μm

100 μm

PROCESS FOR PRODUCING APHIDICOLIN USING THE MICRORGANISM VERTICILLIUM SP

BACKGROUND OF THE INVENTION

1. Field of the Invention

This invention relates to a process for producing aphidicolin, and more particularly to a process for producing aphidicolin by culturing microorganisms.

2. Prior Art

Aphidicolin is a sparingly water-soluble substance having a tetracyclic diterpenetetraol represented by the following formula:

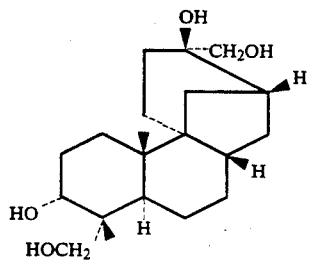

which is obtained from *Verticillium lecanii*, a kind of mold, and has been found to have an antiviral effect. Aphidicolin also has a high specific inhibiting action on DNA polymerase α originating from eucaryotic cells, and thus has been used to identify the type of DNA polymerase originating from eucaryotic cells. Furthermore, aphidicolin has no such effect on DNA polymerase originating from procaryotic cells excluding specific viruses and is used mainly in the analysis of DNA replication and repair mechanisms. Furthermore, aphidicolin is known to have an antitumor effect, an anti-virus effect and a plant seed growth-inhibiting effect and thus its utilization in these fields has been contemplated.

However, aphidicolin has a low production efficiency and thus is commercially available as a very expensive biochemical reagent (for example, the current merket price is 5,500 yen per mg). It is also reported to produce aphidicolin by using other fungi than the *Cephalosporium aphidicola*, for example, *Phoma betae* [Japanese Patent Application Kokai (Laid-open) No. 58-220690], *Harziella entomophila* [Agri. Biol. Chem., 42, No. 8, page 1611 (1978)], *Onychophora coprophila* [Trans. Br. Mycol. Soc., 83, No. 1, page 149 (1984)], *Nigrospora sphaerica* [Can. J. Microbiol., 20, page 416 (1974)], etc., but their productivity of aphidicolin is low and not satisfactory. For example, only 120 mg of aphidicolin is isolated from 1.5 l of a culture medium of *Nigrospora sphaerica*.

SUMMARY OF THE INVENTION

An object of the present invention is to provide a process for producing aphidicolin with a high productivity by culturing microorganisms.

DETAILED DESCRIPTION OF THE INVENTION

The object of the present invention can be attained according to a process for producing aphidicolin by culturing microorganisms belonging to the genus Verticillium, thereby forming and accumulating aphidicolin and recovering the aphidicolin therefrom.

As the microorganisms belonging to the genus Verticillium, a strain KN-04 (FERM BP-3430) separated from the soil (soil attached to mushrooms naturally growing in a clump of bamboos in Gifu City, Japan) in the course for search for biologically active substances produced by fungi and also its artificial mutants, for example, those obtained by such artificial mutation means as ultraviolet rays, X-rays, actinic rays, chemicals, etc. can be used.

The strain KN-04 of the genus Verticillium has the following microbiological properties:

[a] Cultural Characteristics (plate culture at 25° C.)

(1) Potato dextrose agar meadium

Colonies are fast-growing, reaching about 42 mm in diameter in 8 days. Flat, wet colonies with rope-like hyphae, slightly raised radially extend from the colony center towards the periphery. The colony has a circular periphery and projected center with yeast-like growth. It is at first white, later becoming slightly yellow about the center in reverse. The colony has no rugose face and reverse.

(2) Sabourand's agar medium

Colonies are fast-growing, reaching about 38 mm in diameter in 8 days. Wet colonies with rope-like hyphae, slightly raised and radially extended from the colony center towards the periphery. Colony has a circular periphery and projected colony center with yeast-like growth. At first white, later becoming slightly yellow about the colony center in reverse. Colony has no rugose face and reverse.

(3) YpSs agar medium

Colonies show fast-growing, reaching about 40 mm in diameter in 8 days. White cottony colonies with relatively slender and less discrete rope-like hyphae. Colony has a circular periphery and projected center with yeast-like growth. White in reverse side. Colony has no rugose face and reverse.

(4) Czapek's agar medium

Colonies show fast-growing, reaching about 33 mm in diameter in 8 days. White cottony thin colonies with substantially no rope-like hyphae. Colony has a circular periphery and projected colony center with yeast-like growth. White in reverse side. Colony has no rugose face and reverse.

[b] Morphological Characteristics

Hyphae are branched and have a smooth surface and septa, and are single or are aggregated into a rope-like state. Conidiophore is produced on the aerial hypha or vegetative hypha and is formed singly or whirl.

Phialides are solitary or in whirl, arising from conidiophores and have a slightly small tip end and a slightly larger bottom end. Size is variable, usually 15–30×2–4 μm. Conidia are contained in a sticky spore ball formed on the tip end of phialide. Mode of conidium formation is of a phialo type. The form is of a cigar type (or of a bacillus type). Size is variable, usually 3–7×1–2 μm.

As described above, the present strain fails to form a sexual reproduction organ, but forms only a conidiophore as an asexual reproduction organ, and thus belongs to Hyphomycetales of Hyphomycetes of Deuteromycotina. Conidiophore of the present strain is produced singly or branched (FIG. 3), and phialide is produced in whirl locally (FIGS. 1 to 3). Phialoconidia are formed as a sticky spore ball on the tip end of phialide (FIGS. 1 to 3). Thus, it has been found that the present strain belongs to the genus Verticillium [disclosed by J. W. Carmichael et al: Genera of Hyphomycetes, pages 196 and 208, published by The University of Alberta Press, Alberta, Canada (1986) and George L. Barron: The Genera of Hyphomycetes from Soil, page 321, published by The Williams & Wilkins Company, Baltimore, USA (1968)].

Further, indexing on the species level revealed that the present strain resembles *Verticillium lecanii* (synonym of *Cephalosporium aphidicola*) disclosed by Walter Gams: Cephalosporiumartige Schimmelpilze, page 176, published by Gustav Fischer Verlag, Stuttgart (1971). However, comparative culture of the present strain and *Cephalosporium aphidicola* ATCC 28300 under the identical conditions (plate culture at 25° C. on a potato dextrose agar medium) revealed remarkable differences in culture characteristics therebetween. For example, as to the growth speed, the colony of the present strain grew to a diameter of about 42 mm on 8th day, whereas that of *Cephalosporium aphidicola* grew only to a diameter of about 19 mm. Furthermore, the present strain forms a flat, wet colony on which rope-like hyphae radially extend from the center towards the periphery, whereas *Cephalosporium aphidicola* ATCC 28300 forms a raised thick colony in a white velvet state, on which no rope-like hyphae are observed. Other large difference is that the colony of the present strain shows a yeast-like growth at the center, whereas the colony of *Cephalosporium aphidicola* ATCC 28300 shows no discrete characteristic at the center.

Comparative collation of the present strain with known species of the genus Verticillium revealed that there was neither identical species nor subspecies, and thus the present strain can be now presumed to be Verticillium sp. Though the present strain shows morphological characteristics of the genus Verticillium, it has a yeast-like period (FIG. 4) not found in the definition of the genus Verticillium, and thus detailed taxonomical study is still required for more exact taxonomical determination of the species.

[c] Physiological Characteristics (1) Optimum growth temperature is 23° to 28° C., and the present strain is growable at 10° to 35° C.

(2) Optimum growth pH is in the range of 5 to 8, and the present strain is growable in a pH range of 2 to 10.

(3) During culturing on a potato dextrose agar culture medium, aphidicolin crystals may precipitate in the medium.

The strain KN-04 can be cultured according to the ordinary method for culturing fungi, i.e. by stationary culture or by shaking culture. As a culture medium, any of synthetic media, semisynthetic media and natural media can be used, so far as they contain a nutrient source utilizable by the strain.

The medium contains a carbon source such as glucose, maltose, sucrose, dextrin, glycerin, starch, potato broth, saw dusts, corn meal, etc., a nitrogen source such as soybean powder, cornsteep liquor, cotton seed powder, meat extract, yeast extract, peptones, potato broth, casein hydrolyzate, dried yeast, rice bran, ammonium salts, nitrates, etc., and, if necessary, inorganic salts such as sulfates, nitrates, carbonates, phosphates, chlorides, etc. of sodium, potassium, magnesium, calcium, zinc, iron, etc. When the medium is used as a solid medium, the medium further contains a gelling agent such as agar, gelatin, silica gel, gerane gum, atc.

It is generally preferable to conduct culturing under aerobic conditions at a culture temperature of about 20° to about 30° C. and a pH of about 5 to about 8. Culture time depends on composition of a medium, culture temperature, etc., and is usually one week to one month. Aphidicolin can be formed and accumulated in the medium during the culture time.

Aphidicolin formed and accumulated in the medium can be recovered according to an appropriable combination of the ordinary methods for separating and purifying metabolic products from a culture medium of microorganisms.

For example, aphidicolin can be isolated from a solid culture medium by pulverizing the solid culture medium, suspending the pulverized culture medium in a hydrophilic, organic solvent capable of dissolving aphidicolin, for example, methanol, thereby extracting the aphidicolin into the solvent at room temperature or with heating, filtering the extract, concentrating the filtrate to dryness at a temperature below 60° C., and purifying the residues by silica gel column chromatography.

Aphidicolin can be also isolated from a liquid stationary culture medium by concentrating the culture medium (culture liquor) to dryness at a temperature below 60° C., followed by the same steps as in the case of the solid culture medium, except that a step of recrystallizing the residues from a solvent mixture of methanol and water to obtain crude crystals is carried out before the silica gel column chromatography.

Aphidicolin can be produced with a high productivity by culturing a microorganism, strain KN-04 (FERM BP-3430) belonging to the genus Verticillium in the culture medium.

BRIEF DESCRIPTION OF THE DRAWINGS

FIG. 1 and 2 show sketches based on direct observation of slide culture, respectively, FIG. 3 is a sketch based on preparate observation of slide culture and FIG. 4 is a sketch based on preparate observation of colony center (yeast-like region).

PREFERRED EMBODIMENTS OF THE INVENTION

Figure 1:
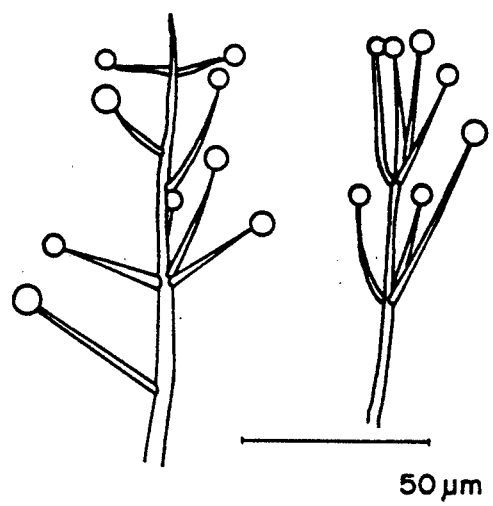
FIG. 1 to 4 show microscopic characteristics of Verticillium sp., where
Figure 2:
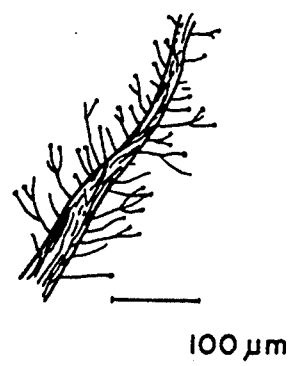
Figure 3:
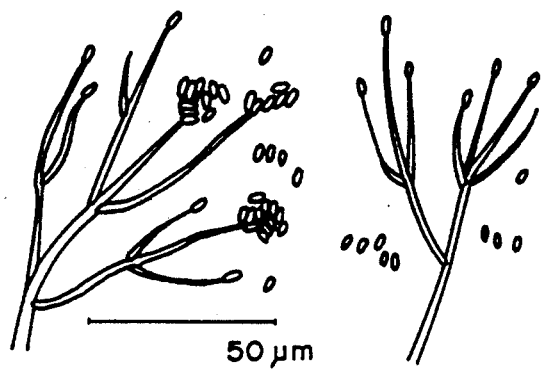
Figure 4:
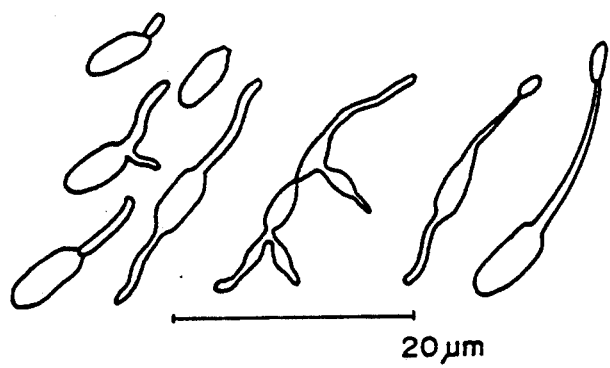

The present invention will be explained in detail below, referring to Examples.

EXAMPLE 1

A slant culture of strain KN-04 of the genus Verticillium was inoculated on 30 ml of seed culture medium (prepared by suspending 39 g of potato dextrose agar culture medium made by Eiken Kagaku K. K., Japan, in 1 l of distilled water, followed by filteration to remove insoluble agar and sterilization in an autoclave at 120° C. for 15 minutes) in a 200-ml flask and subjected to shaking culture at 25° C. for 3 days. Then, 100 μl of the resulting culture liquor was inoculated on 10 ml of culture medium (prepared by suspending 39 g of potato dextrose agar culture medium, made by Eiken Kagaku Kogyo K. K., Japan, in 1 l of distilled water, followed by sterilization in an autoclave at 120° C. for 15 minutes and pouring 10 ml by 10 ml into Petri dishes while hot) in the Petri dishes (each 9 cm in diameter and 15 mm deep) and subjected to stationary culture at 25° C. for 20 days.

The thus cultured medium (625 ml) was pulverized and refluxed in 2 l of methanol with heating for 3 hours. After cooling, the resulting mixture was filtered and the filtrate was concentrated to dryness at a temperature below 60° C. The thus obtained residue was purified by silica gel column chromatography (Wako Gel C-300, a product made by Wako Junyaku K. K., Japan; eluant: chloroform/methanol), and then the eluate was recrystallized from ethanol to give 905 mg of colorless needles of aphidicolin (melting point: 237° to 239° C.). The product was identified by compairing its IR spectrum, mass spectrum, thin layer chromatography and optical rotation with those of authentic specimen of aphidicolin (made by Wako Junyaku K. K., Japan).

EXAMPLE 2

The seed culture (100 μl) obtained in Example 1 was inoculated on 40 ml of liquid medium (the same as the seed culture medium) in a 500-ml flask and subjected to stationary culture at 25° C. for 20 days.

The thus cultured medium (80 ml) was concentrated to dryness at a temperature below 60° C. The thus obtained residue was purified by column chromatography and recrystallized from ethanol to give 24 mg of colorless, needles of aphidicolin, which was identified by comparing with an authentic specimen of aphidicolin.

What is claimed is:

1. A process for the production of aphidicolin comprising culturing Verticillium sp. FERM BP-3430 in a nutrient medium containing assimilable sources of carbon and nitrogen until a substantial amount of aphidicolin is produced and recovering the aphidicolin.

* * * * *